United States Patent [19]

Schulz et al.

[11] 4,105,855

[45] Aug. 8, 1978

[54] MANUFACTURE OF SYMMETRICAL CAROTENOIDS

[75] Inventors: Bernhard Schulz, Schwetzingen; Joachim Paust, Neuhofen; Joachim Schneider, Ludwigshafen, Germany

[73] Assignee: BASF Aktiengesellschaft, Ludwigshafen, Germany

[21] Appl. No.: 652,190

[22] Filed: Jan. 26, 1976

[30] Foreign Application Priority Data

Feb. 12, 1975 [DE] Fed. Rep. of Germany ....... 2505869

[51] Int. Cl.$^2$ .................. C07C 3/00; C07C 13/28; C07C 67/00
[52] U.S. Cl. ................................. 560/190; 260/405; 260/586 R; 260/586 C; 260/601 R; 260/611 V; 260/615 A; 260/666 C; 260/666 PY; 260/668 R; 560/202; 560/259; 568/824
[58] Field of Search ........... 260/485 R, 666 C, 617 B, 260/488 R, 488 A, 666 PY, 668 R, 586 R, 586 C, 601 R, 615 A, 611 V; 560/259, 190, 202

[56] References Cited

FOREIGN PATENT DOCUMENTS 1,148,542  5/1963  Fed. Rep. of Germany ....... 260/666 C

OTHER PUBLICATIONS

Bestmann et al., Chemische Berichte, 96, pp. 1899–1908 (1963).
Denney et al., J. Org. Chem. 28 (1963) pp. 778–780.
Nurrenbach et al., Ann. 721, pp. 34–42 (1969).

*Primary Examiner*—Jane S. Myers
*Attorney, Agent, or Firm*—Keil, Thompson & Shurtleff

[57] ABSTRACT

Symmetrical carotenoids are prepared from the half-molecules by dimerizing the phosphonium salts of the half-molecules with peroxides, peroxo compounds or peroxy compounds in an alkaline medium.

8 Claims, No Drawings

MANUFACTURE OF SYMMETRICAL CAROTENOIDS

There are numerous methods of synthesis for the manufacture of carotenoids, and, inter alia, β-carotene is of particular interest. The conventional processes are not always satisfactory, in particular in respect of the yields, in respect of the starting compounds required, some of which are difficult to manufacture, and in respect to the reaction conditions to be maintained, such as exclusion of water and oxygen or maintenance of low temperatures, which entail expense.

German Pat. No. 1,068,709 discloses a process for the manufacture of β-carotene, based on the principle of a $C_{20} + C_{20}$ synthesis, from axerophthylphosphonium salt and vitamin A-aldehyde in a Wittig reaction, in a substantially anhydrous solvent and under a stream of nitrogen, with exclusion of atmospheric oxygen. A disadvantage of this process is, inter alia, that vitamin A-aldehyde, which has a great tendency to undergo chemical reactions and is not simple to manufacture industrially, is used as the starting material.

H. J. Bestmann and O. Kratzer, Chemische Berichte, 96 (1963), 1899 et seq. disclose that phosphine-alkylenes, which are manufactured from the phosphonium salts under the conditions of the Wittig reaction, can be dimerized by the action of oxygen, with elimination of triphenylphosphine oxide and formation of a double bond. The use of this reaction for the manufacture of β-carotene from triphenylphosphine-axerophthylene is disclosed in German Pat. No. 1,148,542, and gives only a 35% yield of crude carotene. A publication in Liebigs Annalen der Chemie, 721 (1969), 34 et seq. also confirms that when this dimerization, using oxygen or air, is applied to the manufacture of β-carotene or carotenoids, the yields are unsatisfactory. D. B. Denney, J. Org. Chem. 28 (1963), 778 et seq. discloses that acylmethylenephosphoranes can be dimerized with peracetic acid, triphenylphosphine oxide being eliminated and a double bond formed. Denney was unable to dimerize, with peracetic acid, phosphoranes which do not have a carbonyl group in the β-position to the phosphorus atom, e.g. triphenylbenzylidenephosphorane.

We have now found a process for the manufacture of symmetrical carotenoids from the half-molecules, in which the phosphonium salts of the half-molecules are dimerized in a solvent, with the formation of a double bond, by addition of a peroxide, a peroxo compound or a peroxy compound, and a base.

The reaction according to the invention can be represented schematically as follows for the case of β-carotene:

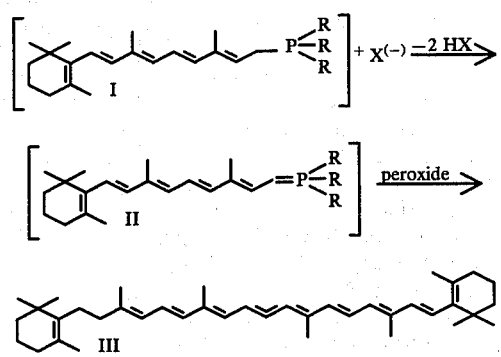

The details of the reaction mechanism are not yet fully understood. However, it is assumed that the reaction takes place via phosphorane or ylid intermediates, such as are known from the Wittig reaction.

In the equation, the R's are identical or different aromatic radicals, especially phenyl, and $X\ominus$ represents the radical of an inorganic or organic strong acid, e.g. bisulfate, halide, especially chloride, bromide or iodide, tetrafluoborate, phosphoate, sulfate, acetate, toluenesulfonate and benzenesulfonate. Of course other acid radicals which are inert under the reaction conditions are also suitable.

The phosphonium salts for the symmetrical carotenoids to be synthesized in accordance with the process of the invention are known compounds or can be obtained, e.g., from the corresponding alcohols or esters by processes described in the literature, e.g. in accordance with German Pat. Nos. 1,068,709 or 1,158,505, or in accordance with the instructions in Houben-Weyl, volume XII/1, pages 79 et seq. (Verlag G. Thieme Stuttgart (1963)).

The preferred phosphonium salts are substituted or unsubstituted triarylphosphonium salts, especially the triphenylphosphonium salts, tricyclohexylphosphonium salts or tributylphosphonium salts, preferred anions being bisulfate and halides, especially chloride and bromide. Bisulfate is the particularly preferred anion.

Symmetrical carotenoids in the content of the present ivention are hydrocarbons (carotenes) and their oxidized derivatives (xanthophylls) which are built up of 8 isoprenoid units in such a way that the isoprenoid units in the center of the molecule are oppositely arranged, so that the two central methyl groups are in the 1,6-position and the remaining non-terminals methyl groups are in the 1,5-position to one another. In the center of a carotenoid there is a chain of conjugated double bonds. All carotenoids can formally be derived from the open-chain structure of lycopene ($C_{40}H_{56}$), e.g. by cyclizations, such as the formation of cyclohexyl and cyclopentyl rings, by dehydrogenations, such as the formation of acetylene bonds and aromatic rings, by hydrogenations, such as hydrogenations of double bonds, by oxidation reactions, such as the formation of alcohols, aldehydes, ketones or acids and the corresponding derivatives, e.g. etherified and esterified alcohols, acetals, ketals or acid esters, by rearrangements, such as the formation of aromatic rings, or by degradation reactions to carotenoids of up to 10 carbon atoms which, e.g., contain aldehyde or acid ester groups as end groups in the molecule. Of course, the said reactions may be carried out in parallel or successively.

Degraded compounds are regarded as carotenoids as long as the two central methyl groups remain preserved (cf. O. Isler, Carotenoids, pages 852 et seq., Birkhauser Verlag Basel and Stuttgart 1971).

In particular, the process according to the invention relates to the manufacture of carotenoids of from 10 to 40 carbon atoms in the isoprenoid skeleton, and preferably of carotenoid compounds of from 20 to 40 carbon atoms. The carotenoid compounds contain a number of conjugated double bonds, as a rule from 3 to 11 and preferably from 7 to 11. In certain cases, two of these double bonds may be modified to triple bonds.

Examples of phosphonium salts of half-molecules are: axerophthytriphenylphosphonium bisulfate for the manufacture of β-carotene, 3,7,11,15-tetramethyl-hexadeca-2,4,6,8,10,14-hexaen-1-yl-triphenylphosphonium bisulfate for the manufacture of lycopene, 5-(2',6',6'-trimethyl-cyclohex-1'-en-1'-yl)-3-methyl-penta-2,4-dien-1-yl -triphenylphosphonium bisulfate for the manufacture of 1,10-bis-(2',6',6'-trimethyl-cyclohex-1'-en-1'-yl)-3,8-dimethyl-deca-1,3,5,7,9-pentaene, 3,7,11,15-tetramethyl-hexadeca-2,4,6,8,10-pentaen-1-yl-triphenylphosphonium bisulfate for the manufacture of 1,2,1',2'-tetrahydrolycopene, 9-(2',6', 6'-trimethyl-4'-methoxy-cyclohex-1'-en-1'-yl)-3,7-dimethyl-2,4,6,8-nonatetraene-1-yl-triphenylphosphonium) bisulfate for the manufacture of zeaxanthin-dimethyl-ether, 9-[2', 3', 4'-trimethyl-phenyl-1']-3,7-dimethyl-nona-2,4,6,8-tetraen-1-yl-triphenylphosphonium bisulfate for the manufacture of renierapurpurine, 9-carbomethoxy-3,7-dimethyl-nona-2,4,6,8-tetraen-1-yl-triphenylphosphonium bromide for the manufacture of methylbixin, 11-carbethoxy-3,7-dimethyl-dodeca-2,4,6,8,10-pentaen-1-yl -triphenylphosphonium bromide for the manufacture of 4,4'-diapocarotene-4,4'-diacid diethyl ester, 8,8-dimethoxy-3,7-dimethyl-octa-2,4,6-trien-1-yl-triphenylphosphonium bromide for the manufacture of crocetin-bis-acetal, from which crocetindialdehyde is obtained by hydrolysis, 3-ethoxycarbonyl-but-2-en-1-yl-triphenylphosphonium chloride for the manufacture of 12,12'-diapocarotene-12,12'-diacid diethyl ester and 7-ethoxy-carbonyl-3-methyl-octa-2,4,6-trien-1-yl-triphenylphosphonium bromide for the manufacture of crocetin diethyl ester.

Further examples to be mentioned are: 9-[2',6',6'-trimethylcyclohex-1'-en-1'-yl]-3,7-dimethyl-nona-2,6,8-trien-4-in-1-yl-triphenylphosphonium bromide for the manufacture of 11,11'-didehydro-β-carotene, 9-[2',6',6'-trimethyl-4'-acetoxy-cyclohex-1'-en-1'-yl]-3,7-dimethyl-nona-2,4,6,8-tetraen-1-yl-triphenylphosphonium bisulfate for the manufacture of zeaxanthin diacetate, which after elimination of the acetyl groups gives zeaxanthin, 9-[2',6',6'-trimethyl-3'-acetoxy-cyclohex-1'-en-1'-yl]-3,7-dimethyl-nona-2,4,6,8-tetraen-1-yl-triphenylphosphonium bisulfate for the manufacture of isozeaxanthin diacetate, which after elimination of the acetyl groups gives isozeaxanthin, 9-[2',6',6'-trimethylcyclohex-1'-en-3'-on-1'-yl]-3,7-dimethyl-nona-2,4,6,8-tetraen-1-yl-triphenylphosphonium bromide for the manufacture of canthaxanthin, 9-[2',6',6'-trimethyl-4'-acetoxy-cyclohex-1'-en-3'-on-1'-yl]-3,7-dimethyl-nona-2,4,6,8-tetraen-1-yl-triphenylphosphonium bromide for the manufacture of astaxanthin diacetate, which after elimination of the acetyl groups gives astaxanthin, 9-[2',5',5'-trimethyl-cyclopent-1'-ene-3',4'-dion-1'-yl]-3,7-dimethyl-nona-2,4,6,8-tetraen-1-yl-triphenylphosphonium bromide for the manufacture of violerythrin and 4,4-dimethoxy-3-methyl-but-2-en-1-yl-triphenylphosphonium chloride for the manufacture of 2,7-dimethyl-2,4,6-octatriene-1,8-bis-dimethylacetal, from which 2,7-dimethyl-2,4,6-octatriene-1,8-dialdehyde is obtained by hydrolysis.

The reaction is carried out in a solvent. Suitable solvents are monohydric and polyhydric lower alcohols, e.g. methanol, ethanol, propanol, isopropanol, isobutanol, glycol and glycerol, chlorinated hydrocarbons, especially methylene chloride, chloroform and carbon tetrachloride, aliphatic and aromatic hydrocarbons, e.g. naphtha, hexane, heptane, benzene and toluene, cycloaliphatic hydrocarbons, e.g. cyclohexane, straight-chain and cyclic acid amides of lower aliphatic carboxylic acids, e.g. dimethylformamide or N-methylpyrrolidone, hexamethylphosphotriamide, acetonitrile, dimethylsulfoxide, sulfolane or water and mixtures of the said solvents, especially mixtures with water. The solvent mixtures may also be two-phase mixtures if, e.g., this circumstance results from the solubility of the particular solvent in water. A very suitable organic solvent is isopropanol. The preferred solvent is water.

Examples of two-phase solvent mixtures are benzene/water, methylene chloride/water, chloroform/water and heptane/water. In the case of two-phase solvent mixtures, the aqueous phase may above all consist of the added aqueous solution of the peroxide or of the peroxo compound or peroxy compound.

Suitable peroxides are hydrogen peroxide or its inorganic or organic derivatives. Examples of suitable inorganic peroxides are alkali metal peroxides and alkaline earth metal peroxides, such as disodium peroxide and barium peroxide. Examples of suitable organic peroxides are alkyl hydroperoxides, such as cumene hydroperoxide, tert.-butyl hydroperoxide, 1,4-diisopropyl-benzene dihydroperoxide, pinane hydroperoxide, dialkyl peroxides, such as di-tert.-butyl peroxide, di-aralkyl peroxides, such as dicumene peroxide, and diacyl peroxides, such as dibenzoyl peroxide and dilauroyl peroxide.

Advantageous peroxo compounds to be used are peroxoacids and their salts, e.g. peroxoborates, peroxophosphates, peroxodiphosphates, peroxocarbonates, peroxodisulfates and peroxosulfates.

Suitable peroxy compounds are monoperoxycarboxylic acids and diperoxycarboxylic acids, their esters and their salts, e.g. peroxyformic acid, peroxyacetic acid, peroxypropionic acid, peroxybenzoic acid, which can optionally be substituted in the phenyl ring, e.g. 3-chloroperoxybenzoic acid, diperoxyphthalic acid or butyl peroctoate. If the reaction is carried out with the phosphonium salt in an aqueous medium, peroxyacetic acid is a very suitable peroxy compound.

As a rule, from 0.8 to 5 moles of peroxide, peroxo compound or peroxy compound are used per mole of phosphonium salt.

Suitable amounts to use are from 1 to 3 moles, especially in an aqueous medium, but a larger excess also does not interfere with the reaction. At times it may be of advantage to use a slightly less than stoichiometric amount of peroxide, especially if an organic solvent in which the carotenoid remains dissolved is used. Where diperoxycarboxylic acids or their salts are used, half the stated molar amounts suffice.

The preferred peroxide is hydrogen peroxide in the form of from 3 to 50 percent strength by weight, especially from 30 to 50 percent strength by weight, aqueous solutions. Further examples of particularly suitable peroxides are disodium peroxide, tert.-butyl hydroperoxide and dibenzoyl peroxide, and especially cumene hydroperoxide. Exampes of particularly preferred peroxo compounds are sodium percarbonate and sodium perborate.

Suitable bases used as proton acceptors are ammonia, ammonium carbonate, alkali metal carbonates, such as sodium carbonate and potassium carbonate, alkali metal hydroxides and alkaline earth metal hydroxides, such as sodium hydroxide, potassium hydroxide and barium hydroxide, alkali metal alcoholates, such as sodium methylate or potassium methylate, sodium ethylate or potassium ethylate, alkali metal amides, such as sodium amide and potassium amide, and monoalkylamines, dialkylamines and trialkylamines wherein alkyl is of 1 to 4 carbon atoms, such as methylamine, diethylamine, triethylamine and tributylamine.

In general, at least an amount of base equivalent to the phosphonium salt, and up to a 200% excess of base, is used. Even a larger excess of base does not interfere with the reaction. Sufficient base is added to convert the phosphonium salts used into the assumed reactive ylid intermediate.

When water or aqueous solvent mixtures are used, the preferred bases include sodium carbonate and potassium carbonate, which are added as solids or, expediently, in the form of aqueous solutions, and ammonia, which can be passed into the mixture as a gas or is expediently used in the form of an aqueous solution of from 10 to 30% strength.

When non-aqueous solvents are used, the preferred bases are gaseous ammonia or the above alkylamines, especially methylamine, alkali metal alcoholates and alkali metal amides. It is superfluous to add a base if the medium reacts alkaline as a result of the addition, or reaction, ofthe peroxo compound or of the peroxide, e.g. of an alkali metal peroxide.

The temperature range in which the reaction is carried out may vary within wide limits, namely from $-50°$ to $+100°$ C. Temperatures of from $-20°$ to $+60°$ C are preferred.

As a rule, the process according to the invention is carried out by suspending or dissolving the phosphonium salt in the solvent used, e.g. isopropanol, methylene chloride, heptane or water. The mixture is then brought to the preferred temperature, namely from $-20°$ to $+30°$ C when using organic solvents and from $0°$ to $+60°$ C when using water.

The peroxy compound or peroxo compound or the peroxide, e.g. a 30 percent strength by weight aqueous hydrogen peroxide solution or dibenzoyl peroxide or cumene hydroperoxide, if appropriate dissolved in a solvent, is then added. Thereafter, the base is admixed.

If desired, the peroxy compound or peroxo compound or the peroxide, and the base, can be added simultaneously to the phosphonium salt. However, it is also possible first to produce the assumed ylid intermediate and then to add the peroxo compound or peroxy compound or the peroxide.

When using sodium carbonate, it is advantageous to employ aqueous solutions of from 5 to 15 percent strength by weight. When using ammonia, it is expedient to use from 1 to 5 equivalents of ammonia, preferably from 2 to 4 equivalents.

As a rule, the dimerization reaction has ended after stirring for several hours up to 12 hours and if the reaction is carried out in water a precipitate of the symmetrical carotenoid, which in general is sparingly soluble, and triphenylphosphine oxide forms. In general, the mixture is worked up by filtering off the precipitate, separating the product from the phosphine oxide, for example by treatment with alcohol, and recrystallizing or reprecipitating the symmetrical carotenoid, thus left, from a suitable solvent. In some cases, recrystallization or reprecipitation of the carotenoid may even be superfluous.

When using a water-miscible organic solvent, e.g. dimethylformamide or isopropanol, the reaction mixture can be partitioned, during working-up, between water and a water-immiscible solvent, e.g. heptane or toluene, so that the carotenoid remains in the water-immiscible phase and inorganic salts and triphenylphosphine oxide remain in the aqueous phase. Further triphenylphosphine oxide can be removed from the water-immiscible phase by washing the latter with, e.g., from 50 to 80% strength aqueous methanol or from 50 to 80% strength aqueous dimethylformamide. On concentrating the purified water-immiscible phase, the carotenoid crystallized out; alternatively, it is precipitated by treatment with solvents in which it is insoluble or sparingly soluble.

When the reaction is carried out in a water-immiscible solvent, e.g. heptane or toluene, the reaction mixture can be worked up similarly by washing the mixture with water and/or with, e.g., from 50 to 80% strength aqueous methanol or from 50 to 80% strength aqueous dimethylformamide, so that the carotenoid remains in the water-immiscible phase and inorganic salts and triphenylphosphine oxide pass into the aqueous phase, after which the procedure described above is followed.

An isomerization to the desired alltrans form of the carotenoid can be carried out by conventional methods, if desired or required. In the case of $\beta$-carotene, such an isomerization can be effected, e.g, by several hours' heating of a $\beta$-carotene suspension in aliphatic hydrocarbons, e.g. in heptane.

The invention alia, a new and technically exceptionally advantageous process for the manufacture of symmetrical carotenoids. It was not to be expected that the reactive unsaturated starting compounds and end products would not undergo side-reactions in the presence of peroxides. A special and surprising advantage is, inter aia, that the process can be carried out in water or in aqueous solutions whilst water is generally detrimental to, e.g., the conventional processes entailing the reaction of phosphonium salts by the Wittig reaction. A further advantage is that the symmetrical carotenoid is obtained in a very pure and finely crystalline form and in very high yields, of up to 90%, especially if the reaction is carried out in water. In an industrial embodiment of the process of the invention, it is even possible to use the residual mother liquors from the synthesis of vitamin A, which contain a high proportion of cis-isomers, as starting material for the axerophthylphosphonium salt for the manufacture of $\beta$-carotene. The ability to react the phosphonium salts in aqueous solution provides an exceptionally advantageous means of removing by-products which have been formed during the manufacturing process or which were present in the starting material, by extracting the aqueous or aqueous-alcoholic solution or suspension of the phosphonium salts which a water-immiscible solvent, e.g., heptane. The aqueous solution or suspension can then in general immediately be reacted further.

By these means it is possible, e.g., to utilize industrially the residual liquors from the synthesis of vitamin A, which can otherwise only be partially worked up, by involved and expensive processes, to give all-trans-vitamin A.

The carotenoids obtained by the process according to the invention may be used as pharmaceuticals, feedstuff additives and dyes for foods and cosmetics.

EXAMPLE 1

63 g of axerophthyltriphenylphosphonium bisulfate are suspended in 30 ml of isopropanol and cooled to from $-5°$ to $-10°$ C, whilst stirring. 20 ml of 30 percent strength by weight aqueous hydrogen peroxide are added and thereafter 0.3 mole of ammonia is passed in in the course of one hour. To complete the reaction, the mixture is stirred for three hours at room temperature. To work up the mixture, 200 ml of 10% strength sulfuric acid are added dropwise. The $\beta$-carotene which has crystallized out is filtered off together with the ammonium sulfate and triphenylphosphine oxide which have precipitated. The product is taken up in methylene chloride and the solution is washed with water. Methanol is then added dropwise and the β-carotene which crystallizes out is filtered off. Yield: 12 g = 45% of β-carotene of melting point 178° C.

EXAMPLE 2

63 g of axerophthyltriphenylphosphonium bisulfate are introduced into 300 ml of methylene chloride. The solution is allowed to cool to from −5° to −10° C and 30 ml of 30 percent strength by weight hydrogen peroxide are added. 0.4 mole of ammonia is then passed in in the course of one hour. The reaction solution is worked up by washing it with water and precipitating the β-carotene with methanol. Yield: 7.5 g of β-carotene = 28%.

EXAMPLE 3

200 ml of isopropanol are cooled to from −10° to −15° C and 0.4 mole of ammonia is then passed in. A mixture of 63 g of axerophthyltriphenylphosphonium bisulfate in 300 ml of isopropanol, 20 ml of water and 10 ml of 30 percent strength by weight hydrogen peroxide is added dropwise. After about 30 minutes, 200 ml of heptane are added, the excess ammonia is stripped off in vacuo, the residue is then acidified with 50 ml of 10% strength sulfuric acid and 150 ml of water are added. After separating off the aqueous phase, the β-carotene suspended in heptane is washed with water and repeatedly with aqueous methanol. The heptane phase is concentrated and the β-carotene is suspended in 50 ml of methanol and filtered off. Yield: 6.5 g of β-carotene = 24.2%.

EXAMPLE 4

32 g of axerophthyltriphenylphosphonium bisulfate are added to 200 ml of water. The mixture is cooled to from 0° to +5° C and after adding 5 ml of 30 percent strength by weight aqueous hydrogen peroxide solution, 100 ml of 10% strength sodium carbonate solution are introduced dropwise. The mixture is then stirred for three hours at room temperature. 200 ml of ethyl acetate are then added and the mixture is washed with water, rendered slightly acid and again washed neutral. About 300 ml of methanol are added to the ethyl acetate solution obtained and the β-carotene which precipitates is filtered off. Yield: 9.5 g = 71%.

EXAMPLE 5

32 g of axerophthyltriphenylphosphonium bisulfate are dissolved in 200 ml of methylene chloride, 5.5 g of solid dibenzoyl peroxide are added and 0.15 mole of ammonia is passed in at −15° C. The mixture is stirred for three hours at room temperature. The methylene chloride solution is washed neutral with water and is concentrated, and the residue is crystallized from ethanol, to give β-carotene. Yield: 1.5 g of β-carotene = 11.2%.

EXAMPLE 6

32 g of axerophthyltriphenylphosphonium bisulfate are dissolved in 200 ml of water, the mixture is cooled to from 0 to +5° C, 5 ml of 30 percent strength by weight hydrogen peroxide are added and 100 ml of 10% strength sodium carbonate solution are then slowly added dropwise. The precipitate which forms and which consists of triphenylphosphine oxide and β-carotene is filtered off, washed repeatedly with warm water and suspended in 200 ml of methanol, and the suspension is heated. After cooling, the pure β-carotene is filtered off and washed with methanol. Yield: 12.8 g, corresponding to 95%, based on the phosphonium salt employed.

$\lambda_{max}$: 450 and 478 nm, in hexane. $E_1^1 = 2,410$ at 450 nm.

EXAMPLE 7

32 g of axerophthyltriphenylphosphonium bisulfate are suspended in 300 ml of water. A suspension of 22 g of sodium perborate in 400 ml of water is added dropwise whilst stirring and cooling the mixture with ice. After stirring for 12 hours, the mixture is worked up as described in Example 6. Yield: 8.8 g of β-carotene, corresponding to 65%, based on the phosphonium salt employed.

$\lambda_{max}$: 450 nm in hexane; $E_1^1 = 2,300$.

EXAMPLE 8

42 g of axerophthyltriphenylphosphonium bisulfate are introduced into 210 ml of water and 25 g of acetic acid containing 34 percent by weight of peroxyacetic acid are added. 150 ml of a 25 percent strength by weight aqueous sodium carbonate solution are added dropwise over the course of one hour at 10° C. After 2 hours, the mixture is extracted with methylene chloride. The methylene chloride solution contains 5.4 g of β-carotene corresponding to a yield of 30 percent based on phosphonium salt employed. The β-carotene was identified, and determined, by means of its UV spectrum.

$\lambda_{max}$: 482 and 454 nm; $E_1^1 = 2,500$ at 453 nm in cyclohexane.

EXAMPLE 9

62.8 g (0.1 mole) of axerophthyltriphenylphosphonium bisulfate are dissolved in 200 ml of dimethylformamide and 21.7 g (0.1 mole) of m-chloroperoxybenzoic acid are added. The reaction mixture is cooled to −15° C and at this temperature 0.4 mole of ammonia is passed in. The reaction mixture is then warmed to 0° C and stirred for a further 30 minutes, at 30° C. It is then taken up in chloroform. The absorbance of the solution in cyclohexane is determined and compared with that of the pure product. $E_1^1 = 2,500$ (455 nm) in cyclohexane. From this it follows that the yield of β-carotene is 0.81 g (3%). $\lambda_{max}$: 455 nm in cyclohexane.

EXAMPLE 10

3,7,11-Trimethyl-dodeca-1,4,6,10-tetraen-3-ol is prepared in accordance with German Pat. No. 1,115,238 from pseudoionone by reaction with sodium acetylide in liquid ammonia, followed by hydrogenation of the triple bond. The phosphonium bisulfate is prepared therefrom in the conventional manner, according to German Pat. No. 1,068,710, by reaction with triphenylphosphine and sulfuric acid. This phosphonium salt is reacted with β-formylcrotyl acetate, in accordance with German Pat. No. 1,068,710, to give 1-acetoxy-3,7,11,15-tetramethyl-hexadeca-2,4,6,8,10,14-hexaene. Crystalline 3,7,11,15-tetramethylhexadeca-2,4,6,8,10,14-hexaen-1-yl-triphenylphosphonium bisulfate is prepared from this ester, in accordance with German Pat. No. 1,068,709, by reaction with triphenylphosphine and sulfuric acid. Melting point 150° – 155° C.

8 g of this triphenylphosphonium bisulfate are dissolved in 70 ml of water; 30 ml of 30 percent strength by weight hydrogen peroxide are added and 10 percent strength by weight aqueous sodium carbonate solution is then added dropwise whilst stirring. The temperature rises to +30° C. The mixture is then stirred for three hours at room temperature. The precipitated triphenylphosphine oxide and the lycopene are filtered off and washed with warm water. The residue is suspended in ethanol, the suspension is stirred at room temperature and the product is filtered off. The crystals are washed with methanol and dried. Yield: 1.5 g = 42% of lycopene. $\lambda_{max}$: 501, 470, 441 and 294 in hexane.

EXAMPLE 11

Axerophthyltriphenylphosphonium bisulfate is prepared from 32.8 g of vitamin A-acetate by the conventional method, in accordance with German Pat. No. 1,068,709. The phosphonium salt obtained is dissolved in 500 ml of water. 100 ml of 30 percent strength by weight aqueous hydrogen peroxide solution are then added. 200 ml of 10 percent strength by weight aqueous sodium carbonate solution are then added dropwise at from 20° to 25° C and the mixture is stirred at room temperature for a further three hours. The precipitate is then filtered off and washed repeatedly with warm water, at 50° – 60° C, to free the precipitate from salt. The $\beta$-carotene and triphenylphosphine oxide are suspended in 200 ml of methanol and the suspension is heated whilst stirring. After it has cooled, the pure $\beta$-carotene is filtered off. Yield: 16 g = 70%, based on vitamin A-acetate employed.

$\lambda_{max}$: 450 and 478 nm in hexane; $E_1^1 = 2,400$ at 450 nm; $E_1^1 = 320$ at 335 nm.

EXAMPLE 12

33 g of axerophthyltriphenylphosphonium bisulfate are introduced into 600 ml of water. 25 ml of 30 percent strength by weight aqueous hydrogen peroxide solution are added at 5° C. A solution of 6.7 g of sodium hydroxide in 90 ml of water is then added dropwise, whilst stirring. The batch is stirred for 12 hours. After filtering off the precipitate, 2.8 g of $\beta$-carotene, i.e. 21% yield, are isolated using methanol.

EXAMPLE 13

29 g of 5-[2',6',6'-trimethyl-cyclohex-1'-en-1'-yl]-3-methylpenta-2,4-dien-1-yl-triphenylphosphonium bisulfate are dissolved in 200 ml of water, the solution is cooled to from 0° to 5° C and 30 ml of 30 percent strength by weight aqueous hydrogen peroxide are added. 100 ml of 10 percent strength by weight aqueous sodium carbonate solution are then added in the course of half an hour. The mixture is stirred for three hours at room temperature. It is then worked up by decanting the water from the precipitate, adding 200 ml of heptane and 200 ml of methanol and, when all has dissolved, separating off the lower phase, containing phosphine oxide, and after adding 50 ml of water, twice extracting the mixture with 100 ml of heptane. The combined heptane solutions are extracted with a mixture of 60 parts by volume of methanol and 40 parts by volume of water. 5 g of 1,10-bis-[2',6',6'-trimethylcyclohex-1'-en-1'-yl]-3,8-dimethyl-deca-1,3,5,7,8-pentaene are obtained from the heptane solution. Yield 50%, based on phosphonium salt employed.

$\lambda_{max}$: 374 nm in hexane; Melting point 136° – 141° C.

EXAMPLE 14

32 g of axerophthyltriphenylphosphonium bisulfate are added to 300 ml of water. The mixture is cooled to from 5° to 10° C and a suspension of 22 g of sodium percarbonate in 300 ml of water is added dropwise. After stirring for 12 hours, the mixture is worked up as described in Example 6. Yield: 10 g of $\beta$-carotene, i.e. 75% based on phosphonium salt employed.

$\lambda_{max}$: 450; $E_1^1 = 2,300$ in hexane.

EXAMPLE 15

65.6 g of vitamin A-acetate are dissolved in 65 ml of heptane. This solution is added dropwise, in accordance with German Pat. No. 1,158,505, to a solution of 52.5 g of triphenylphosphine and 7.6 g of hydrogen chloride in 130 ml of heptane and 170 ml of isopropanol and the mixture is stirred for 12 hours at room temperature. 200 ml of water are added, the heptane phase is separated off and the aqueous phase is extracted four times with 200 ml of heptane. A further 340 ml of water are then added, the mixture is cooled to 5° C, and 100 ml of 30 percent strength by weight hydrogen peroxide are admixed. 400 ml of a 10 percent strength by weight sodium carbonate solution are added dropwise in the course of half an hour whilst stirring and the whole is stirred for 3 hours at room temperature. The precipitated triphenylphosphine oxide and $\beta$-carotene are filtered off and washed with methanol and then with water at 70° C. The $\beta$-carotene thus obtained is suspended in 200 ml of methanol, the suspension is refluxed for fifteen minutes and cooled, and the product is filtered off. Yield: 10.4 g, i.e. 19% based on vitamin A-acetate employed.

$\lambda_{max}$: 450 nm; $E_1^1 = 2,110$ in hexane.

EXAMPLE 16

62.8 g (0.1 mole) of axerophthyltriphenylphosphonium bisulfate in 300 ml of isopropanol are cooled to −15° C and 18.2 g of technical-grade cumene hydroperoxide solution, corresponding to 0.09 mole of pure cumene hydroperoxide, are added. 0.3 mole of ammonia is then passed into the reaction mixture in the course of one hour at −15° C. The mixture is allowed to warm up to 0° C and is then stirred for half an hour at 30° C, after which 100 ml of heptane and 200 ml of water are added. The aqueous lower phase is separated off and the heptane phase, which contains the $\beta$-carotene substantially in a suspended form, is washed once with 250 ml of water and twice with 250 ml each time of a 60% strength methanol/water mixture. Residual water and methanol are distilled azeotropically from the heptane phase. On filtering the cooled suspension, 15.8 g (65.5%) of all-trans-$\beta$-carotene are obtained.

$E_1^1 = 2,480$ in cyclohexane; $\lambda_{max}$: 455 nm.

EXAMPLE 17

62.8 g (0.1 mole) of axerophthyltriphenylphosphonium bisulfate in 200 ml of isopropanol are cooled to −15° C and 12.1 g of technical-grade tert.-butyl hydroperoxide solution, corresponding to 0.1 mole of pure tert.-butyl hydroperoxide, are added. 0.25 mole of ammonia is passed into the reaction mixture of −15° C in the course of one hour; the mixture is then kept for 30 minutes at 0° C, after which it is warmed to 30° C for 1.5 hours. Following this, the reaction mixture is taken up in chloroform and the absorbance of the solution in cyclohexane is determined and compared with that of the pure procuct, $E_1^1 = 2,500$ (455 nm) in cyclohexane. The results indicate a yield of 7.4 g (28%) of β-carotene. $\lambda_{max}$: 455 nm in cyclohexane.

EXAMPLE 18

1 part by weight of triphenylphosphine is suspended in 4 parts by weight of methanol. 0.37 part by weight of sulfuric acid is added dropwise in the course of 15 minutes, whilst stirring, and thereafter 2.44 parts by weight of a vitamin A-acetate residual mother liquor from the industrial synthesis of vitamin A are added dropwise in the course of 30 minutes. The non-crystallizable residual mother liquor oil contains about 1.5 million international units of vitamin A per gram and is rich in mono- and di-cis-isomers. The temperature is kept below 30° C and stirring is continued for from one to twelve hours at room temperature. After adding 2.48 parts by weight of water, the mixture is extracted four times with, in each case, 1.3 parts by weight of heptane, whereby the heptane-soluble by-products and impurities are removed. The methanol is distilled from the purified phosphonium salt solution in vacuo. The residue is made up to 11.5 parts by weight with water and 0.46 part by weight of 30 percent strength by weight hydrogen peroxide is added. 2.33 parts by weight of a 25 percent strength by weight aqueous sodium carbonate solution are added dropwise in the course of one hour whilst stirring. The temperature is kept below 30° C by cooling. Stirring is continued for a further two hours, the mixture is then heated to from 50° to 60° C and the precipitated phosphine oxide and β-carotene are filtered off and washed repeatedly with warm water. The residue is suspended in 9 parts by weight of methanol and the suspension is refluxed whilst stirring. It is then filtered whilst warm and the crystalline β-carotene which is left is isomerized in 0.8 part by weight of heptane, in the conventional manner, by refluxing for twelve hours. After filtering off and drying the product, 0.5 part by weight of all-trans-β-carotene is obtained. Melting point 170° C; $E_1^1 = 2,500$ at 450 nm in cyclohexane.

EXAMPLE 19

5.35 g (10 millimoles) of 7-ethoxycarbonyl-3-methyl-octa-2,4,6-trien-1-yl-triphenylphosphonium bromide (manufactured according to Helv. Chim.Acta 49, 369 (1966)) are stirred up in 50 ml of isopropanol and 2.0 g of a technical-grade cumene hydroperoxide solution, corresponding to 10 millimoles of pure cumene hydroperoxide, are added at $-10°$ C. 50 millimoles of ammonia are passed in at $-10°$ C in the course of half an hour and the reaction mixture is then allowed to return to room temperature. After stirring for a further half hour at 30° C, the mixture is taken up in 100 ml of toluene and the solution is washed with 50 ml of water. The toluene phase is further washed twice with 60% strength aqueous dimethylformamide, dried over sodium sulfate and concentrated, and the residue is finally chromatographed, in ethyl acetate, on 100 g of silica gel, elution being carried out with the same solvent. 1.08 g (56%) of crocetin diethyl ester are obtained from the concentrated eluate.

$\lambda_{max}$: 412, 434 and 462 nm in chloroform; $E_1^1 = 2,100$ at 412 nm; $E_1^1 = 3,250$ at 434 nm; $E_1^1 = 3,090$ at 462 nm.

EXAMPLE 20

10.7 g (0.02 mole) of 7-carbethoxy-3-methyl-octa-2,4,6-trien-1-yl-triphenylphosphonium bromide are suspended in 100 ml of water, the suspension is cooled to 0° C and 6.8 g (0.1 mole) of 50% strength hydrogen peroxide are added. A solution of 5.3 g of sodium carbonate in 50 ml of water is added dropwise to the reaction mixture in the course of 3 hours. The reaction mixture is then stirred for a further 2 hours at room temperature and the precipitate formed is filtered off, and is additionally washed once with hot water, then with a 60% strength methanol/water mixture and finally with pure methanol. 2.6 g (corresponding to 67.7% yield) of crocetin diethyl ester which has been dried in a stream of nitrogen are obtained. $E_1^1 = 1,265$ (412 nm), 1,623 (462 nm), 1,836 (434 nm) in chloroform.

EXAMPLE 21

8,8-Dimethoxy-3,7-dimethyl-octa-2,4,6-trien-1-yl-triphenylphosphonium bromide from 9.82 g (0.02 mole) of 3,7-dimethyl-8-oxo-octa-2,4,6-trien-1-yl-triphenylphosphonium bromide (prepared according to Helv. Chim. Acta. 49, 369 (1966)) are suspended in 100 ml of an 0.1 percent strength by weight aqueous sodium carbonate solution and 6.8 g (0.1 mole) of 50% strength hydrogen peroxide are added. The reaction mixture is cooled to 0° C, a solution of 8.5 g of sodium carbonate in 80 ml of water is added dropwise and the mixture is stirred for a further 5 hours at room temperature. It is then extracted with toluene and methylene chloride, the extract solution is washed twice with a 60% strength methanol/water mixture and concentrated, and the residue is treated with a mixture of 100 ml of methylene chloride, 50 ml of methanol, 100 ml of water and 20 ml of 20% strength sulfuric acid. After 2 hours the organic phase is separated off, washed with water, dried and concentrated. The absorbance of the residue in chloroform is determined and compared with that of the pure product. $E_1^1 = 3,970$ at 455 nm in chloroform.

This indicates that the residue contains 0.71 g (24%) of crocetin dialdehyde. $\lambda_{max}$: 455 and 483 nm in chloroform.

EXAMPLE 22

19.2 g (0.1 mole) of 2,6-dimethyl-8-acetoxy-octa-2,4,6-trienal and 59.5 g (0.14 mole) of 3-ethoxycarbonyl-but-2-en-1-yl-triphenylphosphonium chloride in 300 ml of methylene chloride are stirred with 200 ml of ethylene oxide for 24 hours at room temperature. The excess ethylene oxide and methylene chloride are stripped off in vacuo and the residue is repeatedly extracted with heptane. The combined heptane phases are washed with a 60% strength methanol/water mixture and concentrated. 28.1 g (corresponding to 88% yield) of 2,6,10-trimethyl-12-acetoxy-dodeca-2,4,6,8,10-pentaene-acid ethyl ester are obtained. $^1$H-NMR (CDCl$_3$): δ= 1.3 (t, CH$_3$); 1,95 (m, 4 CH$_3$); 4.2 (9, CH$_2$); 4.75 (d, CH$_2$); 5.7 (t, 1 H); 6-8 (m, 6 H).

21.5 g (0.068 mole) of the crude product are dissolved in 200 ml of ethanol and stirred, in an ice bath, with a solution of 5 g of sodium ethylate in 100 ml of ethanol. After 15 minutes the reaction mixture is diluted with 500 ml of ice water and extracted repeatedly with toluene. The combined toluene phases are washed with water, dried over sodium sulfate and concentrated. The alcohol thus obtained, in 400 ml of anhydrous ether and 0.25 ml of pyridine, is reacted with 6.93 g of phosphorus tribromide in 40 ml of ether at $-20°$ C. The reaction mixture is stirred for a further 30 minutes at $-10°$ C and is then poured into ice water. The aqueous phase is again extracted with ether. The combined ether solutions are washed with ice-cold sodium bicarbonate solution and ice water, dried and concentrated in vacuo. The residue is dissolved in 200 ml of ethyl acetate and the solution is stirred with 15.7 g of triphenylphosphine for 12 hours. The crystals which have precipitated are filtered off and washed with ether. Yield: 16.1 g of 11-carbethoxyh-3,7-dimethyl-dodeca-2,4,6,8,10-pentaen-1-yl-triphenylphosphonium bromide; melting point = 116°- 120° C.

3.0 g (0.005 mole) of the phosphonium salt are dissolved in 50 ml of isopropanol and 1 g of cumene hydroperoxide solution, corresponding to 0.005 mole of pure cumene hydroperoxide, is added. 0.02 mole of ammonia is passed into the mixture at −10° C. The reaaction mixture is then warmed to room temperature, stirred for a further 30 minutes at 40° C and then taken up in toluene, and the toluene solution is washed successively with water and with a 60% strength aqueous dimethylformamide solution. The absorbance of the toluene solution is determined in chloroform and compared with that of the pure product, $E_1^1 = 3,150$ at 502 nm in chloroform. This indicates that the toluene solution contains 0.16 g (12.4%) of 4,4'-diapocarotene-4,4'-diacid diethyl ester. $\lambda_{max}$: 475, 502 and 537 nm in chloroform.

EXAMPLE 23

35.8 g (0.186 mole) of 2,6-dimethyl-8-acetoxy-octa-2,4,6-trienal and 78 g (0.21 mole) of methoxycarbonylmethyltriphenylphosphonium chloride in 300 ml of methylene chloride are stirred with 200 ml of ethylene oxide for 12 hours at room temperature and 12 hours at 35° C. The solvents are stripped off in vacuo and the residue is repeatedly extracted with hexane. The combined hexane phases are washed with 60% strength aqueous methanol and concentrated. 38.4 g (corresponding to 78% yield) of 4,8-dimethyl-10-acetoxydeca-2,4,6,8-tetraene-acid methyl ester are obtained. $^1$H-NMR (CDCl$_3$): $\delta$ = 1.9 (s, 2 CH$_3$); 2.05 (s, CH$_3$); 3.75 (s, CH$_3$); 4.7 (d,CH$_2$); 5.4-7.6 (m, 6 H).

The oil obtained is dissolved in 200 ml of methanol and 30 ml of 30% strength sodium methylate in methanol are added whilst keeping the mixture in an ice bath. After 15 minutes, the mixture is diluted with 200 ml of ice water, neutralized with dilute sulfuric acid and extracted repeatedly with toluene. The alcohol obtained after washing the combined toluene phases with 200 ml of water, drying over sodium sulfate and concentrating is dissolved in 120 ml of naphtha and 180 ml of diethyl ether, and 0.3 ml of pyridine is added. The solution is cooled to −10° C and 8.4 ml of phosphorus tribromide in 30 ml of petroleum ether are added. The mixture is stirred for a further 30 minutes and is then poured into ice water. The aqueous phase is again extracted with ether. The combined ether phases are washed with ice-cold sodium bicarbonate solution and ice water, dried and concentrated in vacuo.

The residue is dissolved in 300 ml of ethyl acetate and 39 g of triphenylphosphine are added. The mixture is stirred overnight and the crystals which have precipitated are filtered off. After recrystallizing them from methylene chloride/ethyl acetate, 42.6 g of 9-carbomethoxy-3,7-dimethyl-nona-2,4,6,8-tetraen-1-yl-triphenylphosphonium bromide are obtained; melting point = 150 -175° C.

10.94 g (0.02 mole) of the phosphonium salt are dissolved in 100 ml of isopropanol and 4 g of technical-grade cumene hydroperoxide solution, corresponding to 0.02 mole of pure cumene hydroperoxide, are added. 0.05 mole of ammonia is passed into the mixture at −10° C. The reaction mixture is then warmed to room temperature, thereafter stirred for 30 minutes at 45° C, and taken up in toluene; the toluene solution is washed successively with water and 60% strength aqueous dimethylformamide solution. The absorbance of the toluene solution in naphtha is determined and compared with that of the pure product, $E_1' = 4,050$ at 456 nm in naphtha. This shows that the toluene solution contains 0.83 g (corresponding to 20% yield) of methylbixin. $\lambda_{max}$: 432, 456 and 490 nm in naphtha.

EXAMPLE 24

42.65 g (0.1 mole) of 3-ethoxycarbonyl-but-2-en-1-yl-triphenylphosphonium chloride are dissolved in 200 ml of ethanol, and 20.4 g of a technical-grade cumene hydroperoxide solution, corresponding to 0.1 mole of pure cumene hydroperoxide, are added at 0° C. 41.95 g of a 24.23% strength sodium ethylate solution in ethanol are added dropwise in the course of 2 hours to the reaction mixture, which is stirred at from 0° to 5° C. The solution is then warmed to room temperature, stirred for 1 hour and mixed with water, and the mixture is extracted with toluene. The toluene phase is concentrated, the residue is taken up in 200 ml of cyclohexane and the solution is extracted with 60% strength aqueous methanol. The organic phase is concentrated and chromatographed over 150 g of silica gel, using a 5:1 cyclohexane/ethyl acetate mixture as the eluant. The eluate is concentrated to give 5.8 g (corresponding to 46% yield) of 12,12'-diaprocarotene-12,12'-diacid diethyl ester. After crystallization from ethanol, the melting point is 90° to 92° C.

EXAMPLE 25

4,4-Dimethoxy-3-methyl-but-2-en-1-yl-triphenylphosphonium chloride is reacted with $\beta$-formylcrotyl acetate in the conventional manner, according to German Pat. No. 1,768,680, to give 8,8-dimethoxy-3,7-dimethyl-octa-2,4,6-triene-1-acetate.

Hydrolysis of this product with aqueous methanolic sulfuric acid gives 2,6-dimethyl-8-acetoxy-octa-2,4,6-trienal which is identical with the product described in Helv. Chim. Acta 49 (1966), 369.

Using the process described in Helv. Chim. Acta 49 (1966), 369, this product is converted to 2,6-dimethyl-8-ol-octa-2,4,6-trienal. 60.5 g of this alcohol, 33.7 g of dihydropyran and 2 drops of concentrated hydrochloric acid are stirred overnight. Excess dihydropyran is evaporated and 2,6-dimethyl-8-(2'-tetrahyropyranyl-)oxy-octa-2,4,6-trienal is obtained. $^1$H-NMR (CDCl$_3$) $\delta$ = 1.1–1.95 (m, 2 CH$_3$, 3 CH$_2$); 3.2–4.0 (m, CH$_2$); 4.2 (d, CH$_2$); 4.6 (s, 1 H); 5.8 (t, 1 H); 6.2–7.5 (m, 3 H); 9.35 (s, 1 H).

Following the method described in J. Chem. Soc. 1963, 5637, 68.8 g (0.145 mole) of 2,3,4-trimethylbenzyl-triphenylphosphonium bromide are suspended in 360 ml of anhydrous ether and treated at −10° C with 94 ml of a 1.62 N butyl-lithium solution in naphtha. The suspension is slowly warmed to room temperature and is then refluxed for 1 hour. The reaction mixture is cooled, 37.5 g (0.15 mole) of 2,6-dimethyl-8-(2'-tetrahydropyranyl-)oxy-octa-2,4,6-trienal are added and the batch is stirred overnight. It is then washed with water and a 60% strength methanol/water mixture and the organic phase is concentrated. The residue is chromatographed over 600 g of silica gel, using a 4:1 cyclohexane/ethyl acetate mixture. The eluates give 43.9 g (corresponding to 83% yield) of 9-[2',3',4'-trimethylphenyl-1']-3,7-dimethyl-1-(2"-tetrahydropyranyl)oxy-nona-2,4,6,8-tetraene. $^1$H-NMR (CDCl$_3$): δ = 1.2–2.35 (m, 5 CH$_3$, 3 CH$_2$); 3.3–3.9 (m, 2 H); 4.15 (d, 2 H); 4.55 (s, 1 H); 5.6 (t, 1H); 5.8–6.7 (m, 5 H); 6.7–7.25 (AB, J = 8 c/s, 2 H).

0.1 mole of this ether of 20 carbon atoms is reacted with 0.1 mole of triphenylphosphine and 0.1 mole of H$_2$SO$_4$ in isopropanol/heptane, in accordance with German Pat. No. 1,068,709 to give 38.1 g of 9-[2',3',4'-trimethylphenyl-1']-3,7-dimethyl-nona-2,4,6,8-tetraen-1-yl-triphenylphosphonium bisulfate. Melting point: 145° – 149° C.

15.6 g (0.025 mole) of the phosphonium salt are suspended in 100 ml of water and 5.1 g (0.075 mole) of 50% strength hydrogen peroxide are added. The solution is cooled to 0° C and a solution of 10.6 g of sodium carbonate in 100 ml of water is added dropwise in the course of 2 hours. The mixture is stirred overnight at room temperature. The crystals which have precipitated are filtered off, washed with hot water, then with methanol, and finally with a little cold heptane. 4.8 g (corresponding to 73% yield of renierapurpurin are obtained. $\lambda_{max}$: 464, 487 and 519 nm in benzene. $E_1^1$ in benzene = 1,590 (487 nm).

EXAMPLE 26

20.6 g (0.82 mole) of 2,6-dimethyl-8-(2'-tetrahydropyranyl)-oxy-octa-2,4,6-trienal in ether and reacted, analogously to Example 21, with 43.6 g (0.1 mole) of 3,7-dimethyl-octa-2-en-1-yl triphenylphosphonium chloride and 0.08 mole of butyllithium. The mixture is washed with water. The ether phase is concentrated, the residue is taken up in heptane and this solution is washed repeatedly with 60% strength methanol and water. After drying and concentrating, 24.6 g (81%) of 3,7,11,15-tetramethyl-1-(2'-tetrahydropyranyl)oxy-hexadeca-2,4,6,8,10-pentaene is obtained as a crude oil. $^1$H-NMR (CDCl$_3$: δ = 0.6–2.2 (m, 5 CH$_3$, 6 CH$_2$, 1 H); 3.3–3.9 (m, 2 H); 4.15 (d, 2 H); 4.51 (s, 1 H); 5.4–6.8 (m, 7 H).

18.6 g (0.05 mole) of this ether of 20 carbon atoms are reacted, in accordance with German Pat. No. 1,068,709, with 0.05 mole of triphenylphosphine and 0.05 mole of H$_2$SO$_4$ in isopropanol/heptane to give the corresponding 3,7,11,15-tetramethyl-hexadeca-2,4,6,8,10-pentaen-1-yl-triphenylphosphonium bisulfate.

The resulting oily salt is dissolved in 100 ml of water without additional purification and 10.2 g (0.15 mole) of 50% strength hydrogen peroxide are added. The solution is cooled to 0° C, a solution of 21.2 g of sodium carbonate in 200 ml of water is added dropwise in the course of 2 hours, and the reaction mixture is stirred for a further 12 hours at room temperature. It is then taken up in 200 ml of heptane. The organic phase is separated off, washed successively with water and 60% strength aqueous methanol, dried and concentrated. The crystals which precipitate on cooling are filtered off. Yield, 1.9 g (14%) of 1,2,1',2'-tetrahydrolycopene. $E_1^1$ in cyclohexane ($\lambda_{max}$): 2,160 (446 nm); 3,270 (474 nm); 2,900 (507 nm.). The mother liquor contains a further 1.6 g (12%) of 1,2,1',2'-tetrahydrolycopene, as measured by UV spectroscopy.

EXAMPLE 27

9 g (0.041 mole) of 4-(2',6',6'-trimethyl-4'-methoxy-1'-cyclohex-1'-enyl)-but-3-en-2-one (prepared according to J. Org. Chem. 32 (1967), 180) in 120 ml of tetrahydrofuran are added dropwise to a solution of 44 millimoles of vinylmagnesium chloride in 100 ml of tetrahydrofuran. After completion of the reaction, the reaction mixture is poured into saturated ammonium chloride solution and the mixture is extracted with ether. The organic phase is repeatedly washed with water, dried and concentrated. The residue of 5-(2',6',6'-trimethyl-4'-methoxy-cyclohex-1'-en-1'-yl)-3-methyl-penta-1,4-dien-3-ol is converted by reaction with 10.8 g (0.041 mole) of triphenylphosphine and 2.2 ml (0.041 mole) of concentrated sulfuric acid by the conventional method, analogously to German Pat. No. 1,068,710 into 5-(2',6',6'-trimethyl-4'-methoxy-cyclohex-1'-en-1'-yl)-3-methyl-penta-2,4-dien-1-yl-triphenylphosphonium bisulfate (22.1 g) of melting point 143° – 146° C. 13.0 g (0.022 mole) of the phosphonium salt and 3.2 g (0.022 mole) of β-formylcrotyl acetate are converted by the conventional method, analogously to German Pat. No. 1,068,710, to 9-(2',6',6'-trimethyl-4'-methoxy-cyclohex-1'-en-1'-1'-yl)-3,7-dimethyl-nona-2,4,6,8-tetraene-1-acetate (6.25 g). $E_1^1$ in cylcohexane = 948 (326 nm).

The last-mentioned compound is reacted, analogously to German Pat. No. 1,068,710, with 4.4 g of triphenylphosphine and 0.9 ml of concentrated sulfuric acid to give 9-(2',6',6'-trimethyl-4'-methoxy-cyclohex-1'-en-1'-yl)-3,7-dimethyl-nona-2,4,6,8-tetraen-1-yl-triphenylphosphonium bisulfate (5.4 g) of melting point 126° – 149° C. $E_1^1$ in isopropanol = 621 (337 nm).

4.7 g (0.0071 mole) of the phosphonium salt thus obtained are suspended in 70 ml of water, 1.7 g of 50% strength hydrogen peroxide are added and the mixture is cooled to 0° C. 5.3 g (0.05 mole) of sodium carbonate in 50 ml of water are added dropwise in the course of 2 hours. The mixture is stirred overnight and the precipitate is filtered off and washed with a large amount of hot water, then with a 60% strength methanol/water mixture and finally with methanol. Yield: 1.07 g (51%) of zeaxanthin dimethyl ether. $\lambda_{max}$: 455 and 483 nm in cyclohexane. $E_1^1$ in cyclohexane = 1,910 (455 nm).

We claim:

1. A process for the manufacture of symmetrical carotenoids from triarylphosphonium salts of the half-molecules of these symmetrical carotenoids, wherein triarylphosphonium salts of the half-molecules are reacted with from 0.8 to 5 times the molar amount of a peroxide, a peroxo compound or a peroxy compound in the presence of a base in water or an aqueous solvent mixture at temperatures of from −50° to +100° C, the half-molecules dimerizing with the formation of a double bond and the elimination of triarylphosphine oxide.

2. A process as claimed in claim 1, wherein an aqueous solution of hydrogen peroxide is used as the peroxide.

3. A process as claimed in claim 1, wherein sodium percarbonate or sodium perborate is used as the peroxo compound.

4. A process as claimed in claim 1, wherein cumene hydroperoxide or tert.-butyl hydroperoxide is used as the peroxide.

5. A process as claimed in claim 1, wherein peroxyacetic acid is used as the peroxy compound.

6. A process as claimed in claim 1, wherein from 1 to 3 moles of peroxide, peroxo compound or peroxy compound are used per mole of phosphonium salt.

7. A process as claimed in claim 1, wherein ammonia or an alkali metal carbonate is used as the base.

8. A process as claimed in claim 1 wherein said triarylphosphonium salts of said half-molecules and the carotenoids produced therefrom are selected from the group consisting of axerophthyltriphenylphosphonium bisulfate for the manufacture of β-carotene, 3,7,11,15-tetramethyl-hexadeca-2,4,6,8,10,14-hexaen-1-yl-triphenylphosphonium bisulfate for the manufacture of lycopene, 5-(2',6', 6'-trimethyl-cyclohex-1'-en-1'-yl)-3-methyl-penta-2,4-dien-1-yl-triphenylphosphonium bisulfate for the manufacture of 1,10-bis-(2',6',6'-trimethyl-cyclohex-1'-en-1'-yl)-3,8-dimethyl-deca-1,3,5,7,9-pentaene, 3,7,11,15-tetramethylhexadeca-2,4,6,8,10-pentaen-1-yl-triphenylphosphonium bisulfate for the manufacture of 1,2,1',2'-tetrahydrolycopene, 9-(2',6',6'-trimethyl-4'-methoxy-cyclohex-1'-en-1'-yl)-3,7-dimethyl-2,4,6,8-nonatetraene-1-yl-triphenylphosphonium) bisulfate for the manufacture of zeaxanthin-dimethyl-ether, 9-[2',3',4'-trimethylphenyl-1']-3,7-dimethyl-nona-2,4,6,8-tetraen-1-yl-triphenylphosphonium bisulfate for the manufacture of renierapurpurine, 9-carbomethoxy-3,7-dimethyl-nona-2,4,6,8-tetraen-1-yl-triphenylphosphonium bromide for the manufacture of methylbixin, 11-carbethoxy-3,7-dimethyl-dodeca-2,4,6,8,10-pentaen-1-yl-triphenylphosphonium bromide for the manufacture of 4,4'-diapocarotene-4,4'-diacid diethyl ester, 8,8-dimethoxy-3,7-dimethyl-octa-2,4,6-trien-1-yl-triphenylphosphonium bromide for the manufacture of crocetin-bis-acetal, from which crocetindialdehyde is obtained by hydrolysis, 3-ethoxycarbonyl-but-2-en-1-yl-triphenylphosphonium chloride for the manufacture of 12,12'-diapocarotene-12,12'-diacid diethyl ester, 7-ethoxy-carbonyl-3-methyl-octa-2,4,6-trien-1-yl-triphenylphosphonium bromide for the manufacture of crocetin diethyl ester, 9-[2',6',6'-trimethylcyclohex-1'-en-1'-yl]-3,7-dimethyl-nona-2,6,8-trien-4-in-1-yl-triphenylphosphonium bromide for the manufacture of 11,11'-didehydro-β-carotene, 9-[2',6',6'-trimethyl-4'-acetoxy-cyclohex-1'-en-1'-yl]-3,7-dimethyl-nona-2,4,6,8-tetraen-1-yl-triphenylphosphonium bisulfate for the manufacture of zeaxanthin diacetate, which after elimination of the acetyl groups gives zeaxanthin, 9-[2',6',6'-trimethyl-3'-acetoxy-cyclohex-1'-en-1'-yl]-3,7-dimethyl-nona-2,4,6,8-tetraen-1-yl-triphenylphosphonium bisulfate for the manufacture of isozeaxanthin diacetate, which after elimination of the acetyl groups gives isozeaxanthin, 9-[2',6',6'-trimethylcyclohex-1'-en-3'-on-1'-yl]-3,7-dimethyl-nona-2,4,6,8-tetraen-1-yl-triphenylphosphonium bromide for the manufacture of canthaxanthin, 9[2',6',6'-trimethyl-4'-acetoxy-cyclohex-1'-en-3'-on-1'-yl]-3,7-dimethyl-nona-2,4,6,8-tetraen-1-yl-triphenylphosphonium bromide for the manufacture of astaxanthin diacetate, which after elimination of the acetyl groups gives astaxanthin, 9-[2',5',5'-trimethyl-cyclopent-1'-ene-3',4+-dion-1'-yl]-3,7-dimethyl-nona-2,4,6,8-tetraen-1-yl-triphenylphosphonium bromide for the manufacture of violerythrin and 4,4-dimethoxy-3-methyl-but-2-en-1-yl-triphenylphosphonium chloride for the manufacture of 2,7-dimethyl-2,4,6-octatriene-1,8-bis-dimethylacetal, from which 2,7-dimethyl-2,4,6-octatriene-1,8-dialdehyde is obtained by hydrolysis.

* * * * *

UNITED STATES PATENT AND TRADEMARK OFFICE
CERTIFICATE OF CORRECTION

PATENT NO. : 4,105,855
DATED : August 8, 1978
INVENTOR(S) : SCHULZ ET AL

It is certified that error appears in the above-identified patent and that said Letters Patent are hereby corrected as shown below:

In claim 8, column 18, line 22, cancel "4+" and substitute --4'--.

Signed and Sealed this

Twenty-fourth Day of April 1979

[SEAL]

Attest:

RUTH C. MASON
Attesting Officer

DONALD W. BANNER
Commissioner of Patents and Trademarks